Dec. 19, 1972 G. H. MACK ET AL Plant Pat. 3,276
CHRYSANTHEMUM PLANT
Filed March 30, 1971
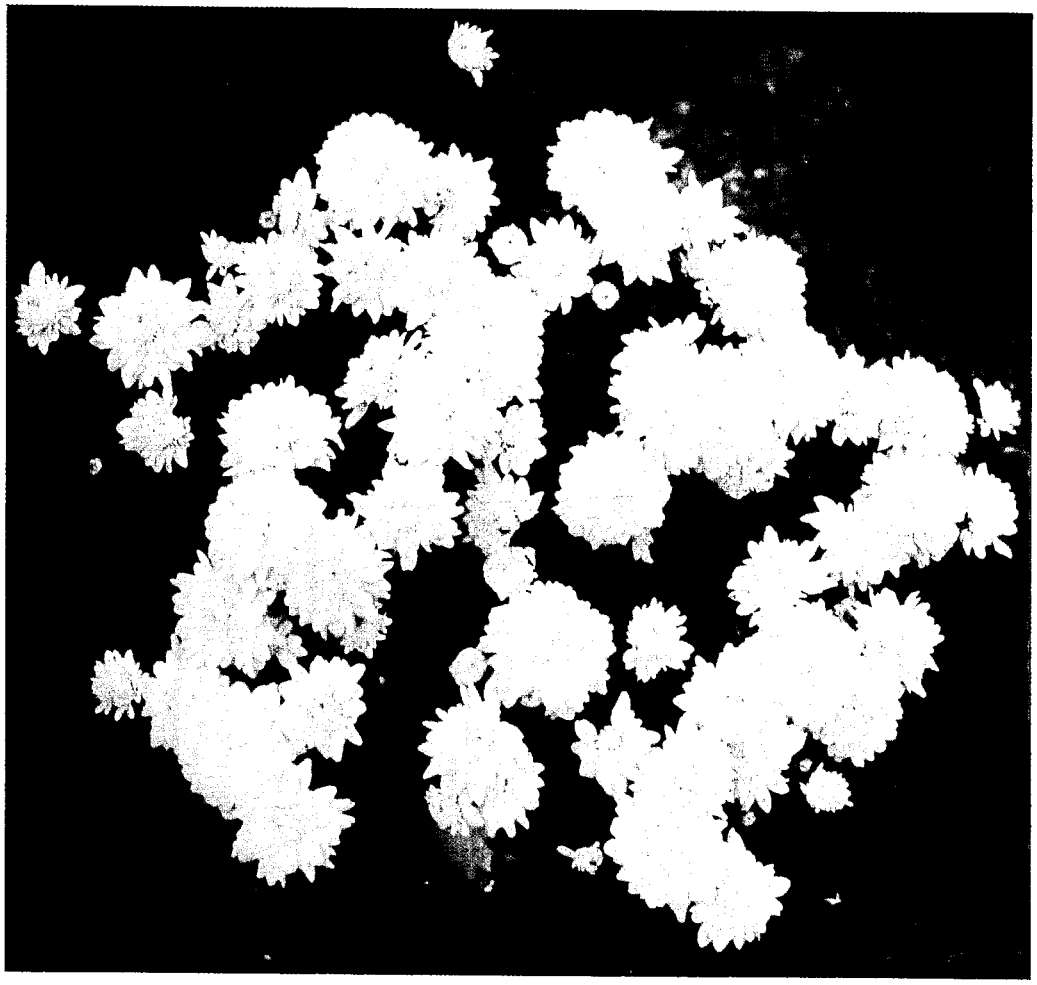
INVENTORS
GRACE H. MACK,
WALTER H. JESSEL, JR.,
WILLIAM E. DUFFETT
BY
Oberlin, Maky, Donnelly & Renner
ATTORNEYS

United States Patent Office

Plant Pat. 3,276

Patented Dec. 19, 1972

3,276

CHRYSANTHEMUM PLANT

Grace H. Mack, New Canaan, Conn., and Walter H. Jessel, Jr., Doylestown, and William E. Duffett, Akron, Ohio, assignors to Grace H. Mack, New Canaan, Conn.

Filed Mar. 30, 1971, Ser. No. 129,648

Int. Cl. A01h *5/00*

U.S. Cl. Plt.—75 1 Claim

The present invention comprises a new and distinct cultivar of chrysanthemum plant which is a seedling of parents identified as #C-8462×#MX598. Both parents are unpatented and are identified for breeding purposes by the above numbers.

The new cultivar is characterized particularly by its early response and its compact cushion habit and is similar in these respects to the cultivar Early Gold, an unpatented cultivar sold commercially by Yoder Brothers, Inc., the assignee of the present invention. In varieties having these characteristics there are relatively few which are generally yellow in color, and the new cultivar fills a definite need in the general grouping indicated.

The new cultivar is distinguished from Early Gold by the following characteristics:

(1) ¾" larger flowers.

(2) Stronger stems.

(3) 6 days longer keeping quality under outdoor garden conditions.

(4) More decorative flower form.

(5) Deeper yellow flower color.

(6) Taller, more spreading, more prolific branching.

(7) Lighter and more deeply indented foliage.

(8) More coarse leaf serration.

(9) More prominent stipules.

(10) Flowers approximately 18 days later in outdoor natural season flowerings.

The new cultivar was asexually reproduced by cuttings at Barberton, Ohio, and has been found to retain its distinctive characteristics through successive propagations.

The new cultivar when grown in the vicinity of Barberton, Ohio, has a response period of approximately 7 weeks, and a natural flowering date of approximately Oct. 3. The following detailed description is based on observations made of the new cultivar both in a greenhouse and outdoors in Barberton, Ohio. The response time, blooming period, color, and total vigor may vary significantly with varying environmental conditions such as temperature, day length, and light intensity. Suggested flowering in the northern and western United States and coastal California is from mid-April through May and mid-September through mid-October.

The accompanying drawing shows the unique characteristics of the new cultivar, the color being as nearly true as possible with color illustrations of this type. In the following description, color references are to the Munsell Color Book, 1963 edition, and comparisons made with the cultivar Early Gold. Where only a single value or designation is given, such value as description applies also to the comparison cultivar.

Botanical classification: *Chrysanthemum morifolium.*

| | Goldtone | Early Gold |
|---|---|---|
| Bloom: | | |
| Size | 2 inches | 1¼ inches. |
| Fully expanded | 2½ inches | 1⅔ inches. |
| Borne | Clusters on elongated pedicels | Clusters on elongated pedicels. |
| Stems | Strong | Moderately strong. |
| Form | Decorative | Intermediate pompon. |
| Permanence | 16 days | 10 days. |
| Color: | | |
| Center of flower | Dark golden yellow 3.75Y8.5/12 | Dark yellow 5Y8.5/12. |
| Base of petals | Dark yellow, 5Y8.5/12 | Do. |
| Inside of petals | do | Do. |
| Reverse of petals | Yellow ,7.5Y8.5/10 | Yellow, 5Y8.5/10. |
| Tonality from a distance | Golden yellow | Golden yellow. |
| Discoloration | Yellow, 5Y5.5/12 | Yellow, 5Y8.5/8. |
| Petals: | | |
| Texture | Smooth | Smooth. |
| Appearance and form | Open at base, broad shallow ridged keel tapering to a blunt point. | Open at base, broad shallow slightly ridged keel tapering to a blunt point. |
| Arrangement | Composite, whorled on a single receptacle | Composite, whorled on a single receptacle. |
| Persistence | Resist shatter | Resist shatter. |
| Fragrance | Typical chrysanthemum | |
| Reproductive organs: | | |
| Stamen, anthers | None-10 | 4-5. |
| Pollen | None-very scant | None. |
| Arrangement | Clustered in center of flower, if present | |
| Styles | Present both ray and disc florets | |
| Length | Short | |
| Ovaries | At the base of petal attached to receptacle | |
| Plant: | | |
| Form | Herbaceous | |
| Growth | Short-spreading | |
| Height | Approximately 11" when flowered naturally as field grown plants from a planting made in mid-June and given a single pinch in late June. | Approximately 8" when flowered naturally as field grown plants from a planting made in mid-June and given a single pinch in late June. |
| Spread | Approximately 19" when flowered naturally as field grown plants from a planting made in mid-June and given a single pinch in late June. | Approximately 14" when flowered naturally as field grown plants from a planting made in mid-June and given a single pinch in late June. |
| Foliage: | | |
| Top side | Dark green, 5GY3/4 | Dark green, 7.5GY3/4. |
| Size | 3½ inches long; 2⅛ inches wide | 2½ inches long; 1½ inches wide. |
| Quantity | Numerous | Numerous. |
| Shape | Spatulate lobed | Spatulate lobed. |
| Texture | Smooth | Smooth. |
| Ribs and veins | Prominent | Prominent. |
| Edge | Deeply indented | Moderately indented. |
| Serration | Coarse | Moderate. |
| Underside | Light green, 7.5GY5/4 | Light green, 7.5GY5/4. |
| Stipules | Rudimentary-prominent | Rudimentary. |

We claim:

1. A new and distinct cultivar of chrysanthemum characterized particularly as to its uniqueness when compared to the known cultivar Early Gold by its ¾″ larger flowers, stronger stems, 6 days longer keeping quality, more decorative flower form, deeper flower color, taller, more spreading, more prolific branching, lighter and more deeply indented foliage, more coarse leaf serration, and more prominent stipules.

No references cited

ROBERT E. BAGWILL, Primary Examiner